United States Patent
Kroemer et al.

(12)

(10) Patent No.: US 6,319,931 B1
(45) Date of Patent: Nov. 20, 2001

(54) USE OF A COMPOUND WITH AFFINITY FOR THE MITOCHONDRIAL BENZODIAZEPINE RECEPTOR IN CANCER THERAPY

(75) Inventors: Guido Kroemer; Tamara Hirsch, both of Paris; Didier Decaudin, Verrieres-le-Buisson, all of (FR)

(73) Assignee: Centre National de al Recherche Scientifique (CNRS), Paris Cedex (FR)

( * ) Notice: Subject to any disclaimer, the term of this patent is extended or adjusted under 35 U.S.C. 154(b) by 0 days.

(21) Appl. No.: 09/332,152

(22) Filed: Jun. 14, 1999

(30) Foreign Application Priority Data

Jun. 22, 1998 (FR) .................................................. 98 07864

(51) Int. Cl.⁷ ........................ C07D 217/00; A61K 45/06; A61K 31/47
(52) U.S. Cl. ............................................. 514/307; 546/144
(58) Field of Search .............................. 546/144; 514/307

(56) References Cited

FOREIGN PATENT DOCUMENTS 0 210 084   1/1987   (EP) .

OTHER PUBLICATIONS

T. Hirsch et al., "PK11195, a ligand of the mitochondrial benzodiazepine receptor, facilitates the induction of apoptosis and reverses Bcl–2–mediated cytoprotection", Experimental Cell Research 6/98, pp 426–434, XP002098088.

*Primary Examiner*—Zinna Northington Davis
(74) *Attorney, Agent, or Firm*—Foley & Lardner (57) ABSTRACT

The present invention relates in particular to a combination product comprising at least one compound with affinity for the mitochondrial benzodiazepine receptor, and to at least one apoptosis-inducing agent for simultaneous or separate use or for use spread out over time, which is intended for the treatment of cancer. Another aspect of the present invention relates to the use of the said compound and/or of the said combination product for the manufacture of a medicinal product intended to facilitate the induction of apoptosis.

9 Claims, 4 Drawing Sheets

USE OF A COMPOUND WITH AFFINITY FOR THE MITOCHONDRIAL BENZODIAZEPINE RECEPTOR IN CANCER THERAPY

The present invention relates in particular to a combination product comprising at least one compound with affinity for the mitochondrial benzodiazepine receptor, and to at least one apoptosis-inducing agent for simultaneous or separate use or for use spread out over time, which is intended for the treatment of cancer. Another aspect of the present invention relates to the use of the said compound and/or of the said combination product for the manufacture of a medicinal product intended to facilitate the induction of apoptosis.

The methods currently used in the treatment of cancer are mainly radiotherapy and chemotherapy. These techniques consist in eradicating the tumor cells identified by means of localized irradiations or by means of pharmacological inducers of cell death. However, these therapeutic approaches are not specific to the tumor cells alone. Indeed, the neighboring tissues are also eradicated and very high toxicity is observed. Considering that the natural programs of cell death (or apoptosis) and senescence no longer function in tumor cells, one approach for treating cancer might lie in re-establishing these programs.

In general, apoptosis is characterized by three phases: an initiation phase in which the various death stimuli take so-called "private" pathways to converge on a common effector phase, which leads finally to the degradation phase characterized by the characteristic biochemical symptoms of cell death. The effector phase is carried out by the mitochondrial permeability transition pore, which is the true sensor of cell death since its open or closed conformations determine the fate of the cells. These different conformations can be induced by many ligands for the components of this permeability transition pore.

The mitochondrial permeability transition pore, commonly known as the mega-channel or multi-conductance channel, participates in regulating the level of calcium in the matrix, the pH and the transmembrane potential ($\Delta\Psi_m$) in the mitochondria. This pore (PT) thus functions as a channel which is dependent on $Ca^{2+}$, the voltage, the pH and the redox potential with several levels of conductance and little selectivity with respect to the ions (Zoratti et al. 1995, Kinnally et al. 1996, Bernardi et al. 1996, and Ichas et al. 1997). Recently, it has been demonstrated that opening of tile PT pore, which is regulated by Bcl-2, is a critical event in the process leading to apoptosis (Kroemer et al. 1997a and 1997b). Opening of the PT pore allows dissipation of the mitochondrial internal transmembrane potential ($\Delta\Psi_m$), the consequence of which is to disrupt the integrity of the outer membrane, leading to the release of mitochondrial intermembrane proteins (Zamzami et al. 1996, Susin et al. 1997a, Kantrow et al. 1997 and Ellerby et al. 1997). In point of fact, the release of intramembrane proteins, such as cytochrome c, and/or the dissipation of the $\Delta\Psi_m$ are common elements of the early phase of apoptosis (Kroemer et al. 1997a and 1997b, Liu et al. 1996, Kluck et al. 1997, Yang 1997 and Susin et al. 1997b). Depending on the experimental system and the cell type, an increase in the volume of the matrix causes either a physical disruption of the outer mitochondrial membrane and then dissipation of the $\Delta\Psi_m$ (Kluck et al. 1997, Yang et al. 1997 and Vander Heiden et al. 1997) or a disruption of the outer membrane and simultaneous dissipation of the $\Delta\Psi_m$ of the inner membrane (Zamzami et al. 1996 and Susin et al. 1996a). Regarding the theoretical aspect, the authors mentioned above have postulated that the increase in the volume of the matrix, which precedes the reduction of the $\Delta\Psi_m$, might be controlled by opening the PT pore. In this sense, the PT pore can operate both at a level of low and reversible conductance (which would give rise to an influx of ions and water into the mitochondrial matrix), and at a level of high and irreversible conductance (which would lead to disruption of the $\Delta\Psi_m$).

The PT pore is a multiprotein complex formed at the site of contact between the inner and outer mitochondrial membranes. Co-localization of the PT pore and of the Bcl-2 oncoprotein is observed (De Jong et al. 1994). The exact molecular composition of this pore remains an enigma. However, it is known that proteins of the cytosol (hexokinase), of the outer membrane (mitochondrial benzodiazepine receptor [mBzR], mitochondrial porin, commonly referred to as the voltage-dependent anion channel), the intermembrane space (creatine kinase), the inner membrane (adenine nucleotide translocator, ANT) and the matrix (cyclophilin D) are involved in the formation of the PT pore and/or in its regulation (Zoratti et al. 1995, Beutner et al. 1996, McEnery 1992, Kinnally et al. 1993, O'Gorman 1997). The PT pore is regulated by multiple endogenous effectors, which is in accordance with its complex composite architecture. Among these effectors are the local ions and the pH gradient, ADP/ATP, NADPH and the molecules involved in transduction of the apoptotic signal, such as $Ca^{2+}$ or oxygen-reactive species. Thus, some of the subunits of the PT pore night constitute pharmacological targets for modulating apoptosis.

Compounds belonging to the isoquinolinecarboxamide family have been described in U.S. Pat. No. 4,801,595 as being useful for the treatment of hypertension, In this family, PK11195 (1-(2-chlorophenyl)-N-methyl-N-(1-methylpropyl)-3-isoquinolinecarboxamide) is known as being a prototypic antagonist ligand for the peripheral benzodiazepine receptor mBzR (Ripond et al. 1991 and Joseph-Liauzun et al. 1997). More particularly, WO 93/11771 relates to the use of molecules such as PK11195 for the treatment of diseases of the central nervous system, in particular trauma.

Now, surprisingly, certain compounds with affinity for the mitochondrial benzodiazepine receptor allow opening of the mitochondrial permeability transition pore, and the experiments which have led to the present invention demonstrate that compounds of formula I, II, III, IV, and V in particular facilitates cell death.

Cancer therapy currently consists in using radiotherapy, chemotherapy or a combination of these. These two methods have harmful side effects which are very poorly tolerated by the patients. Thus, the use of pharmacological agents designed to increase the susceptibility of tumor cells to apoptosis induction is very advantageous, since it allows the use of lower doses of chemotherapy or radiotherapy products, thereby minimizing their side effects. Components with strong affinity for the PT pore subunits, mentioned above, are the subject of the present invention since they facilitate apoptosis and thus allow the use of lower doses of products with strong side effects. This also makes it possible to improve the efficacy of certain treatments.

Thus, no document of the prior art either discloses or suggests the present invention as described below.

DESCRIPTION OF THE INVENTION

Thus, the present invention relates to a combination product comprising at least one compound with affinity for the mitochondrial benzodiazepine receptor, and to at least one apoptosis-inducing agent for simultaneous or separate use or for use spread out over time, which is intended for the treatment of cancer.

The term cancer is used in a broad sense which includes any neoplasia (for example cancers, sarcomas, lymphomas and leukemias).

The said compound is selected from several families of molecules with affinity for the mitochondrial (peripheral) benzodiazepine receptor, preferably from the families of general formulae I, II, III, IV and V described below.

In the isoquinoline family, the molecules chosen in particular are of general formula I:

I in which

R1 is a linear or branched C1–C6 lower alkyl group,

R2 is a linear or branched C1–C6 lower alkyl group,

R3 is a halogen atom such as Cl, F, Br or I, and R4 is a hydrogen or halogen atom, the groups R1, R2, R3 and R4 being chosen independently of each other.

Advantageously, the said compound is PK11195 (commercially available from Sigma under the reference C 0424) corresponding to the following formula: 1-(2-chlorophenyl)-N-methyl-N-(1-methylpropyl)-3-isoquinolinecarboxamide.

PK 11195

This compound was described in Ferry A., 1989, Fund, Clin. Pharmacol., 3, 383 and in Doble A. et al. 1985, Eur. J. Pharmacol., 119, 153.

The molecules chosen in particular are those represented by formula II. Their formulae and the processes for their preparation are described in EP 210,084A1, which is incorporated by way of reference in the description.

II in which

A represents a nitrogen atom or a CH group,

B represents a nitrogen atom or a CH group,

V and W, which may be identical or different, represent hydrogen atoms or halogen atoms (fluorine, chlorine or bromine), alkyl or alkoxy groups comprising 1 to 3 carbon atoms, or nitro or trifluoromethyl groups, Z is fixed in an ortho or para position relative to B and represents a phenyl, thienyl or pyridyl radical, or a phenyl radical substituted with one or two substituents taken from halogen atoms, alkyl and alkoxy groups comprising 1 to 4 carbon atoms, and trifluoromethyl or nitro groups, the chain $—X—(CH_2)_n—(CHR)_m—CONR_1R_2$ is fixed in an ortho or para position relative to B, R represents a hydrogen atom or an alkyl group comprising 1 to 3 carbon atoms, $R_1$ and $R_2$ which may be identical or different, represent a linear or branched alkyl group comprising 1 to 6 carbon atoms, a cycloalkyl group comprising 3 to 6 carbon atoms, a phenyl group, a phenylalkyl or cycloalkylalkyl group in Which the alkyl part comprises 1 to 3 carbon atoms and the cycloalkyl part comprises 3 to 6 carbon atoms, an alkenyl group comprising 3 to 6 carbon atoms on condition that the double bond is not located in position 1,2 relative to the nitrogen atom, $R_1$ and $R_2$ can also form, together with the nitrogen atom to which they are attached, a pyrrolidine, piperidine, morpholine or thiomorpholine ring, X represents a group CH—$R_3$, N—$R_4$, SO or $SO_2$ or an oxygen or sulfur atom, $R_3$ represents a hydrogen atom or an alkyl group comprising 1 to 3 carbon atoms,

$R_4$ represents an alkyl group comprising 1 to 3 carbon atoms, m is equal to 0 or 1, n is equal to 0, 1 or 2, it being understood that when X represents a group SO, $SO_2$ or N—$R_4$, the sum m+n is at least equal to 1, it being understood that when A and B each represent a nitrogen atom and Z is in the para position relative to B, X cannot represent a group CH—$R_3$, it being understood that when A represents a CH group, B represents a nitrogen atom, Z is in an ortho position relative to B, X represents an oxygen atom and R represents a hydrogen atom, the sum m+n is other than 1, with the exception of 2-phenyl-4-quinolyl N,N-dimethylcarbamate, in other words, the compounds of formula (II) correspond to one of the formulae (IIa) and (IIb)

in which A, B, V, W, X, Z, R, R, R, n and m have the meanings given above.

These compounds bind to the peripheral-type benzodiazepine receptors (EP 210 084 page 11, lines 9–10). As compounds which are particularly advantageous, mention may be made in particular of those described from page 11 line 25 to page 13 line 21 of EP 210 084A1.

The molecules chosen in particular are those represented by formula III below. Their formulae and the processes for their preparation are described in EP 248 734B1, which is incorporated by reference in the description.

in which
- $R_1$ and $R_1'$, which may be identical or different, represent C1–C4 alkyl groups containing a linear or branched chain, cycloalkyl groups in which the alkyl part comprises 1 to 3 carbon atoms and the cycloalkyl part comprises 3 to 6 carbon atoms, or phenyl groups,
- $R_1$ and $R_1'$ can also form, with the nitrogen atom to which they are attached, a piperidine ring.
- Ar represents a phenyl or thienyl radical or a phenyl radical substituted with one or two substituents chosen from halogen atoms (fluorine, chlorine or bromine), alkyl or alkoxy groups comprising 1 to 4 carbon atoms, and nitro or trifluorophenyl groups, represents one of the following ring units:

These compounds of formula III are ligands for the peripheral (mitochrondrial) benzodiazepine receptor (EP 248 734B1 page 4 lines 46–54).

The ones chosen in particular are those belonging to formula IV below. Their formulae and the processes for their preparation are described in EP 112 776B1, which is incorporated by reference in the description.

in which $R_1$ is a linear or branched C1–C6 alkyl group, a phenyl group, a C3–C6 cycloalkyl group, a phenylalkyl or cycloalkyl group in which the alkyl radical is C1–C3, or a group in which $R_3$ and $R_4$ are hydrogen atoms or alkyl groups and $R_5$ is an alkenyl or alkynyl group, the sum of the carbon atoms in $R_3$, $R_4$, and $R_5$ being between 2 and 5, $R_2$ is a linear or branched C1–C6 alkyl group, a phenylalkyl or cycloalkyl group in which the alkyl radical is C1–C3, a group in which $R_3$, $R_4$, and $R_5$ are defined as above, or a group in which n is 0, 1, 2 or 3, it being possible for R1 and R2 to form, together with the nitrogen atom to which they are attached, a 5-, 6- or 7-membered heterocyclic radical which can contain another hetero atom chosen from nitrogen and oxygen and which can bear one or two substituents chosen from C1–C3 alkyl, hydroxyl, oxo, hydroxyalkyl or dimethylaminoalkyl groups in which the alkyl part is C1–C3, Z is a phenyl, pyridyl, thienyl or 2-thiazolyl group or a phenyl group substituted with one or two substituents chosen from halogen atoms, C1–C3 alkyl, alkoxy or alkylthio groups, a trifluoromethyl group and a nitro group,

X and Y are identical or different and are hydrogen or halogen atoms, C1–C3 alkyl or alkoxy groups, or nitro or trifluoromethyl groups, A and B are, independently of each other, nitrogen atoms or CH groups, or any stereoisomer of formula IV.

Among these compounds, those described in Examples 8, 10, 15–17, 18, 19–22, 37, 39, 43, and 51 of EP 112 776B1 have particularly high affinity for the mitochondrial benzodiazepine receptor (EP 112 776B1 page 21).

The molecules chosen in particular are those of formula V. Their formulae and the processes for their preparation are described in EP 094 271B1, which is incorporated by reference in the description.

in which,

- $R_1$ and $R_2$ independently represent a linear or branched C1–C6 alkyl group, a C3–C7 cycloalkyl group, a phenylalkyl or cycloalkyl group in which the alkyl part is C1–C3;
- $R_1$ and $R_2$ can also represent a C2–C6 alkenyl or alkynyl group on condition that the double or triple bond is not in position 1–2 relative to the nitrogen atom; $R_1$ and $R_2$ can represent a group of formula —$R_3$—Z—$R_4$ in which $R_3$ is a linear or branched C2–C6 alkylene group on condition that at least two carbon atoms separates the nitrogen atom from the group Z; R4 represents a C1–C4 alkyl group and Z is an oxygen or sulfur atom or a group N—$R_5$, $R_5$ representing a hydrogen atom or a C1–C3 alkyl group;
- R1 and R2 can form, with the nitrogen atom to which they are attached, a heterocycle optionally comprising a second hetero atom,
- Ar represents a phenyl, pyridyl or thienyl group or a phenyl group substituted with one or two substituents chosen from halogen atoms, C1–C4 alkyl, alkoxy and alkylthio groups, a trifluoromethyl group and a nitro group; A and B are, independently, N or CH.

represents the ring unit or, when A is N and B represents CH, one of tile following ring units X and Y independently represent a hydrogen or halogen atom, a C1–C3 alkyl or alkoxy group, or a nitro or thiofluoromethyl group.

The pharmacological properties of these compounds are described on page 11, column 20 and page 12 column 21 of EP 094 271B1. The satisfactory affinity for the mitochondrial benzodiazepine receptor, particularly for the molecules of Examples 1, 10, 16, 25, 32, 35, and 47of EP 094 271B1, is noted.

The expression "apoptosis-inducing agent" denotes any substance which directly or indirectly affects the viability of a cell.

The said apoptosis-inducing agent of the present invention can be selected in particular from agents which damage DNA, glucocorticoid receptor ligands or pro-apoptotic second messengers.

These agents can also be selected from those commonly used in the treatment of cancer. Thus, the said pro-apoptotic second messenger is selected from glucocorticoid derivatives, from alkylating agents such as nitrogen mustards, for example cyclophosphamide, platinum complexes, for example cisplatin, ethyleneimine derivatives, dimethane sulfonoxyalkane derivatives or piperazine derivatives, from topoisomerase inhibitors such as topoisomerase-2 inhibitors, for example anthracyclines, epipodophyllotoxins such as etoposide, topoisomerase-1 inhibitors, for example camptothecin derivatives, from antimetabolites such as antifolates, for example methotrexate, antipurines, for example 6-mercaptopurine, antipyrimidines, for example 5-fluorouracil, from antimitotic agents such as vinca alkaloids, taxoids such as taxol, taxotere, and from various cytolytic agents such as bleomycin, dacarbazine, hydroxycarbamide, asparaginase, mitoguazone and plicamycin.

These antineoplastic agents are descriobed in Actualité Pharmaceutiques No. 302 (October 1992) pages 38 to 39 and 41 to 43, which are incorporated in the description by reference.

Preferably, the said apoptosis-inducing agent is chosen from gamma radiations, etoposide, doxorubicin, dexamethasone, ceramide such as ceramide C8, and lonidamine.

Some of the said anticancer agents are described more particularly in U.S. Pat. No. 5,260,327 which relates to the use of lonidamine for treating metastases, in Official Gazette U.S. Pat. No. 5,017,353 which relates to the use of lonidamine in combination with other anticancer agents, and in EP 291,151, which describes the use of phlorizine derivatives. These documents are incorporated into the description by reference.

The product according to the present invention can also contain a viral vector which contains a gene which codes for an enzyme for activating the abovementioned compounds and/or agents, for example thymidine kinase. Many patents relating to the use of activated suicide genes in specific tissues are found in the family of EP 415,73 1. Among these documents, which are incorporated into the description by reference, are: EP 494,776, EP 690,129, EP 657,540, and EP 657,541 which relate in particular to the manufacture of a medicinal product comprising a vector which contains a gene capable of catalyzing the conversion of a prodrug into the active substance. More particularly, EP 657,539 relates to the use of a thymidine kinase gene with cell specificity for the treatment of cancer.

Similarly, the product of the present invention can also comprise one or more pharmaceutically acceptable vehicles.

In another aspect, the present invention relates to the use of the product described above for the manufacture of a medicinal product intended for the treatment of cancer. In particular, the said medicinal product is intended to induce the death of tumor cells and/or facilitate apoptosis.

The present invention is also directed towards the use of a compound with affinity for is the mitochondrial benzodiazepine receptor for the manufacture of a medicinal product intended for the treatment of cancer, in particular to facilitate the induction of apoptosis. Preferably, it may be chosen to use a compound from the family corresponding to one of the general formulae I, II, III, IV, and V described above, notably from the following molecules:

1-(2-chlorophenyl)-N-methyl-N-(1-methylpropyl)-3-isoquino-linecarboxamide (PK11195),
N,N-diethylcarbamate de phenyl-3 naphtyle-1,
N,N-diethyl α-methyl phenyl-2 quinazoline-4 propanamide,
N-methyl N-phenyl phenyl-2 quinazoline-4 propanamide,
N,N-diethyl (nitro-4 phenyl)-2 quinazoline-4 propanamide,
N,N-diéthyl [(phényl-2 trifluorométhyl-8 quinolinyl-4)oxy]-2 propanamide,
N,N-diethyl (methoxy-3 phenyl)-2 quinazoline-4 propanamide,
N,N-diethyl phenyl-3 isoquinoleine-1 propanamide,
N-methyl N-(methyl-1 propyl) phenyl-7 benzo[b]thiophenecarboxamide-5,
N,N-diethyl phenyl-3 naphtalenecarboxamide-1,
and N-methyl N[methyl-1 propyl] (chloro-2 phenyl)-1 isoquinoleinecarboxamide, -3.

for the manufacture of such a medicinal product.

Bcl-2 is the prototypic representative of the family of apoptosis-inhibiting oncogenes which contributes both to the generation of cancer and which is responsible for the difficulties in eradicating tumors. Most of the cytoprotective effects of Bcl-2 can be attributed to its capacities to protect the integrity of the mitochonidrial membranes (Boise et al. 1997, Reed et al. 1997). It has been shown that Bcl-2 stabilizes mitochondrial membranes in various models of apoptosis (Zamzami et al. 1995, and Decaudain et al. 1997). However, it appears that Bcl-2 does not manage to inhibit apoptosis in certain cases, in particular apoptosis induced by diamide and by activation of caspase (Yasuhara et al. 1997, Strasser et al. 1995, and Huang et al. 1997). The effect of Bcl-2 is also overcome by treatment with a taxoid, such as paclitaxel (taxol), this agent allowing the hyperphosphorylation of Bcl-2 (Haldar et al. 1995 and 1996), and which promotes opening of the PT pore (Evtodienki et al. 1996).

Thus, the present invention proposes an alternative for overcoming the chemo- or radioresistance observed by mediation by Bcl-2. The treatment of cells with a ligand for mBzR makes cytoprotection with Bcl-2 largely obsolete. There is virtual stoichiometry between the expression of Bcl-2 and that of mBzR, at least as regards the lymphoid cell lines (Carayon et al. 1996). In addition, Bcl-2 protects isolated mitochondria against opening of the PT pore induced by low doses of protoporphyrin IX, which is an mBzR ligand, and this inhibition is suppressed by strong doses of protoporphyrin IX (Marchetti et al. 1996a). This suggests that a functional interaction exists between Bcl-2 and mBzR. On the other hand, the protection against opening of the PT pore, controlled by Bcl-2, is not overcome by increasing doses of the other target agents for the PT pore such as atractyloside, which is a ligand for the adenine translocator. Since the binding of mBzR does not bring about any negative regulation of the expression of Bcl-2 (Carayon et al. 1996), it thus seems probable that the conformational changes arising from the binding of PK11195 in the complex composed of mBzR and the PT pore indirectly affects the stability of the mitochondrial membrane and thus overcomes the anti-apoptotic function of Bcl-2. Consequently, the binding of a compound with affinity for the mitochondrial benzodiazepine receptor, belonging to the families I, II, III, IV and V, in particular PK11195, represents an advantageous strategy in particular for overcoming resistance to chemotherapy and to radiotherapy.

In the description hereinbelow, reference will be made to the key for the figures presented below.

BRIEF DESCRIPTION OF DRAWINGS

FIG. 1: Synergism between PK11195 and ceramide for the induction of apoptosis in thymocytes.

The thymocytes were cultured for 4 hours in the presence of $C_8$ ceramide (25 $\mu$M), diazepam (100 $\mu$M) and/or PK11195 (100 $\mu$M).

Graph A represents the level of apoptosis, with the disruption of the $\Delta\Psi_m$ (determined with $DiOC_6$) on the x-axis and the generation of superoxide anion (determined with HE) on the y-axis.

Graph B represents the level of apoptosis, with the exposure of phosphatidylserine at the surface of the plasma membrane (measured with FITC-annexin V) on the x-axis and the cell viability (exclusion of ethydium bromide) (EthBr) on the y-axis. The numbers denote the percentages of cells found in each quadrant.

The cells were cultured with 10 $\mu$M etoposide, 1 $\mu$M dexamethasone (DEX), RU24858, RU38486, and/or with 75 $\mu$M PK11195, either for 12 hours or for 24 hours. This graph represents the determination of the frequency of $DiOC_6$ $(3)^{low}$ (HE→Eth)$^{low}$, $DiOC_6$ $(3)^{low}$ (HE→Eth)$^{high}$ and hypoploid cells as described in the examples. The asterisks indicate a substantial and significant (p<0.01) enhancement in the induction of apoptosis by PK11195 compared with the control cultures (cultured in the absence of PK11195).

The cell line of 2B4.11 T-cell hybridomas transfected stably with a vector SFFV.neo containing the human Bcl-2 gene (graph B) or containing only the neomycin (neo)—resistance gene (graph A) were cultured for 12 hours in the presence of dexamethasone (1 $\mu$M), PK11195 (50 $\mu$M) or diazepam (50 $\mu$M), and the parameters associated with apoptosis, mentioned above, were determined. The numbers in the black circles indicate the frequency of the sub-diploid cells. The synergistic effect of PK11195+DEX is very significant (p<0.01) compared with the controls (treatment with DEX or PK11195 alone). Similar results were obtained when dexamethasone is replaced with etoposide as apoptosis-inducing agent.

The WEHI 231 cells, either transfected with the control neomycin vector (neo, graph A) or transfected with a vector containing the human Bcl-2 gene (graph B), were treated by γ-irradiation, with doxorubicin (doxo), cyclosporin A (CsA), alone or in combination with PK11195 (40 $\mu$M) or with diazepam (40 $\mu$M). These graphs show the determination, by flow cytometry, of the apoptosis parameters indicated. The asterisks show a significant effect (p<0.001) of PK11195.

PK11195 facilitates the induction of apoptosis by a variety of stimuli.

Figure 1A:
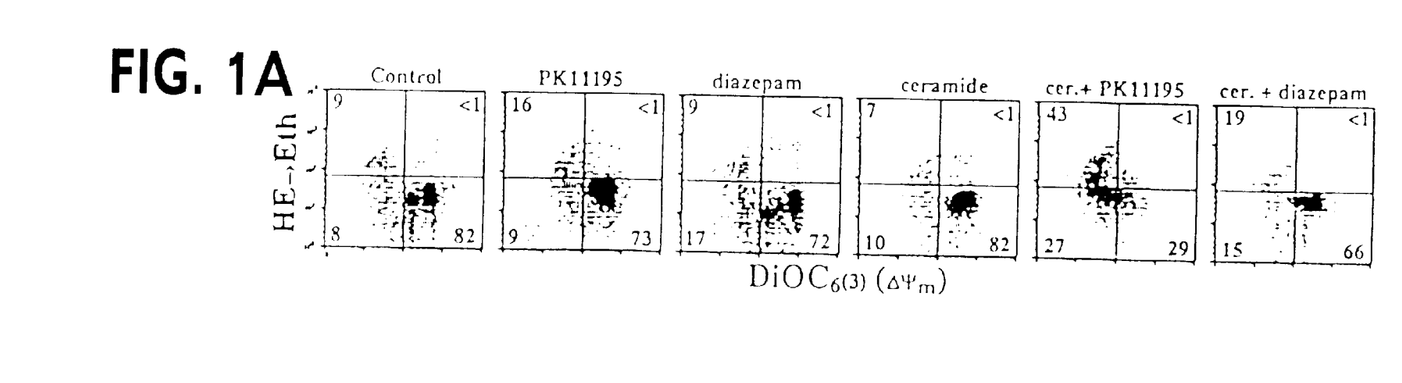
Figure 1B:
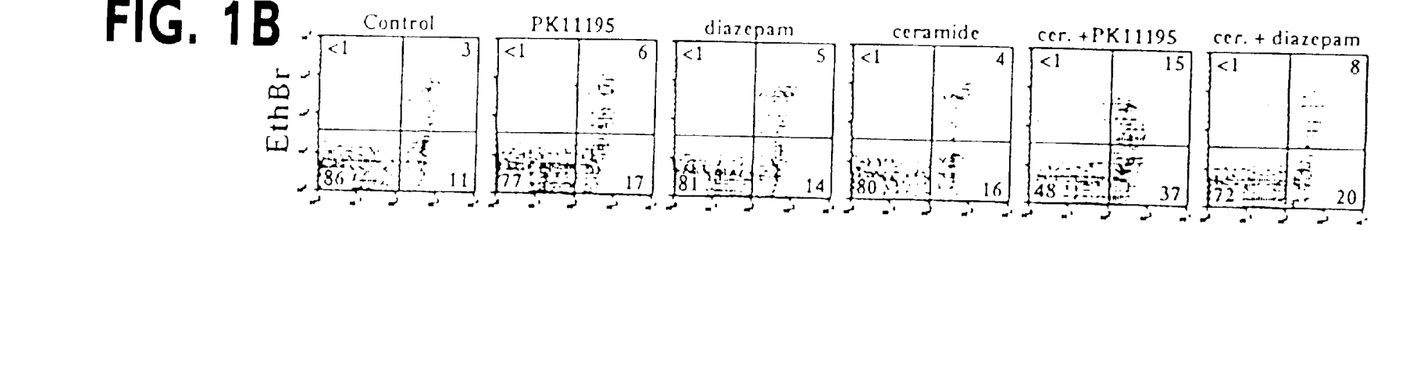
Figure 2:
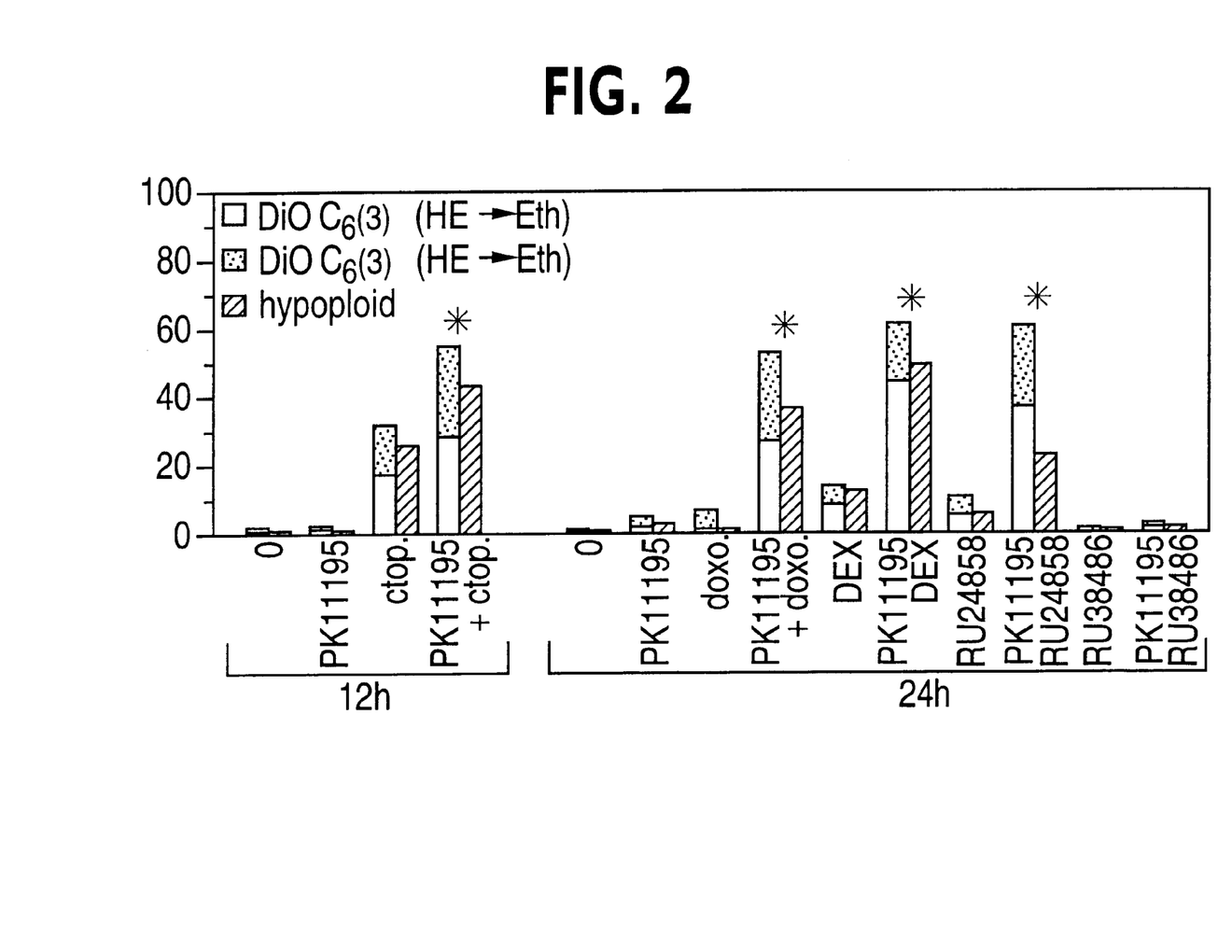
FIG. 2: PK11195 facilitates the induction of apoptosis in the CEM-C7 T-cells of acute leukemia.
Figure 3A:
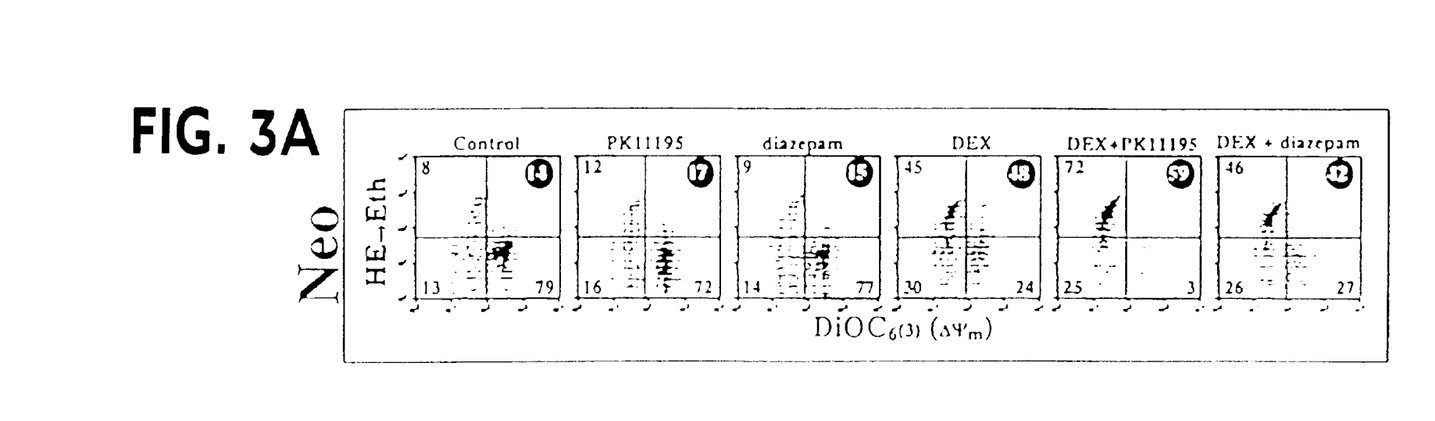
FIG. 3: PK11195 opposes the cytoprotection obtained by mediation of Bcl-2 in T-cell hybridomas.
Figure 3B:
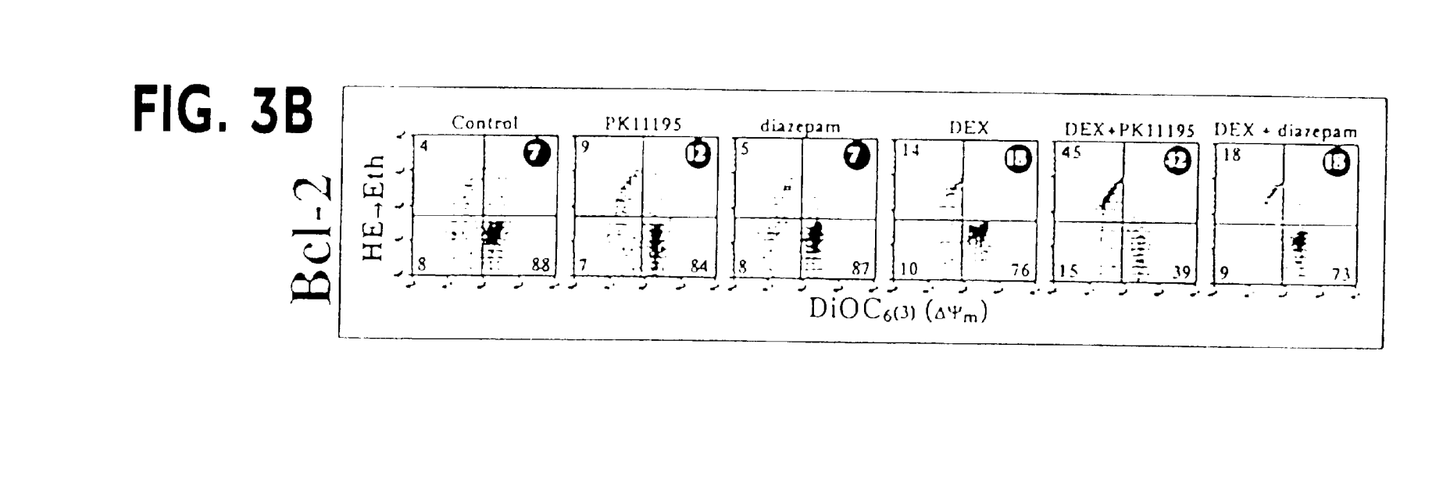

PK11195 is the prototypic antagonist ligand for the mitochondrial benzodiazepine receptor mBzR (Ripond et al. 1991 and Joseph Liauzun et al. 1997). Up to doses of 50 to 100 $\mu$M, PK11195 shows no toxic effect on various cell types comprising, in particular, thymocytes (see FIG. 1), CEM-C7 T-cells of acute leukemia (see FIG. 2), 2B4.11 T-cell hybridomas (see FIG. 3) and leukemic WEHI231 B-cells (see FIG. 4). The results of the experiments carried out during the present invention demonstrate that ceramide C8, which by itself induces no apoptosis of thymocytes (at a dose of 25 µM), becomes apoptogenic in the presence of PK11195. On the other hand, diazepam, which is an agonist acting on the central mitochondrial benzodiazepine receptor, has no significant apoptogenic effect (see FIGS. 1, 3 and 4). Among the various ligands for mBzR which were tested, PK11195 appears to be the most effective of the apoptosis co-inducers (relative efficacy: PK11195 greater than 4'-chlorodiazepam≧diazepam>Ro-5-4864); this result correlates with the antagonist potential of these compounds on the mBzR receptor (Zisterer et al. 1997).

Figure 4A:
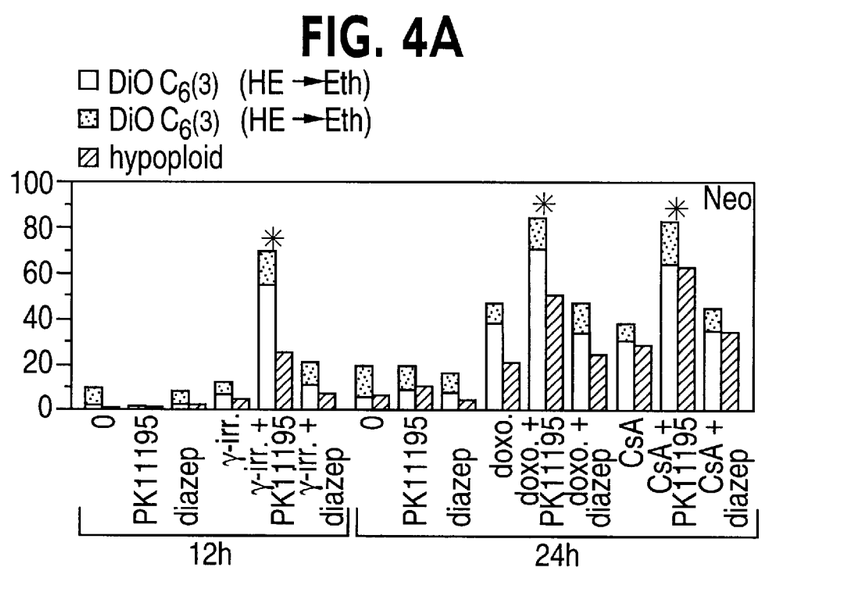
FIG. 4: PK11195 enhances the susceptibility to apoptosis in leukemic WEHI 231 B-cells which overexpress Bcl-2.
Figure 4B:
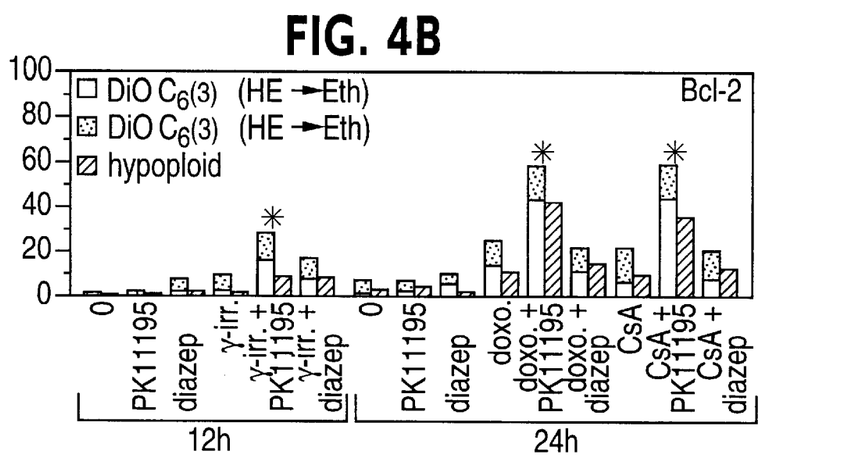

The synergistic tests observed with PK11195 extend to a variety of different apoptosis inducers, in particular with the topoisomerase II inhibitor (etoposide, see FIG. 2), γ-irradiation (see FIG. 4), the doxorubicin-intercalating agent (see FIG. 4) and, as regards the WEHI231 cells, cyclosporin A (see FIG. 4). In addition, PK11195 (but not diazepam) facilitates the induction of apoptosis by glucocorticoid receptor agonists (which comprise dexamethasone and RU24858) (see FIG. 2). On the other hand, no effect was revealed during the use of RU38486 and PK11195 simultaneously. Thus, PK11195 facilitates the induction of apoptosis in response to a very wide variety of substances and in many different cell types, in particular in primary and transformed cell lines of human and murine origin (see FIGS. 2 to 4).

PK11195 facilitates the induction of mitochondrial and post-mitochondrial changes associated with apoptosis Synergism between PK11195 and several pro-apoptotic agents extends to everything which characterizes the phenomenon of apoptosis. These phenomena comprise the early loss of the mitochondrial transmembrane potential (measured using the potential-sensitive dye $DiOC_6(3)$, the increase in the generation of oxygen-reactive species (measured by conversion of hydroethidine into ethidine catalyzed by superoxide anions) (see FIGS. 1 to 4), the exposure eradicates phosphatidylserine residues at the surface of the plasma membrane, measured using annexin V conjugate to FITC (see FIG. 1), and the fragmentation of nuclear DNA (hypoploidy determined by staining, using propidium iodide, of cells fixed in ethanol (see FIGS. 1 to 4)). The experimental techniques mentioned above are described in greater detail in Marchetti et al. 1996a, Kroemer et al. 1997a and 1997b and Zazami et al. 1996) which are incorporated in the present description by reference.

PK11195 overcomes the inhibition of apoptosis controlled by Bcl-2 in several different cell lines.

Bcl-2 possesses cytoprotective effects by virtue of its broad spectrum of action (Kroemer et al. 1997b and Decaudain et al. 1997). Thus, the overexpression of Bcl-2 very significantly prevents the disruption of $\Delta\Psi_m$, the production of superoxide anions, and the nuclear apoptosis induced by dexamethasone in T-cell hybridomas (see FIG. 3). Simultaneous treatment with PK11195 and apoptogenic agent shows a hyperadditive effect which facilitates apoptosis even in the presence of Bcl-2. Thus, PK11195 makes it possible to restore the induction of apoptosis in cells which overexpress Bcl-2 at least partially. This effect was observed in two different cell types, namely 2B4.11 T-cell hybridomas (see FIG. 3B) and leukemic WEHI231 B-cells (see FIG. 4B).

PK11195 makes it possible to overcome the protection conferred by Bcl-2 against glucocorticoids (see FIG. 3B), against γ-irradiation, doxorubicin, cyclosporin A (see FIG. 4B) and etoposide. This effect is also observed as regards the mitochondrion, the cell redox potential and the nuclei (see FIGS. 3 and 4). Thus, the present invention relates to a novel strategy for enhancing the suceptibility of cells by the induction of apoptosis. The compounds of the isoquinolin-ecarboxamide family, in particular an antagonist ligand which is specific for the mitochondrial benzodiazepine receptor (PK11195), facilitates the induction of disruption of $\Delta\Psi_m$ by various apoptotic effectors, in particular damage to DNA (γ-irradiation, etoposide, doxorubicin), the binding of ligands to the glucocorticoid receptor (dexamethasone, RU24858), and pro-apoptotic second messengers of the ceramide type, such as ceramide C8. Concomitantly, the compounds of the isoquinolinecarboxamide family enhance the induction of standard apoptosis signals such as the exposure of phosphatidylserine at the surface of cells and the fragmentation of nuclear DNA. It has been demonstrated that the mitochondrial benzodiazepine receptor interacts with many proteins involved in the formation and/or regulation of the PT pore (McEnery et al. 1992 and Kinnally et al. 1993). In addition, PK11195 facilitates opening of the PT pore induced by a tumor necrosis factor (TNF-α) in L929 cells (Pastorino et al. 1996). In this model, TNF induces necrosis (Schulze-Osthoff et al. 1994) and the necrosis induction is enhanced with PK11195. However, the present invention shows that PK11195 facilitates the induction of apoptosis, which correlates with the induction of dissipation of $\Delta\Psi_m$ controlled by the PT pore. These results suggest that opening of the PT pore might be the limiting step of any cell death (apoptosis and necrosis), (Kroemer et al. 1997a), and that the post-mitochondrial events end with activation of the catabolic enzymes (caspases, proteases other than the caspases, and nucleases) and/or that the bioavailability of extramitochondrial ATP directs the mode of cell death (Hirsch et al. 1997, Leist et al. 1997 and Nicotera et al. 1997).

Thus, the results of the experiments carried out in the present invention demonstrate the strong association between the mitochondria, the redox potential, the plasma membrane and the characteristics of apoptosis, and demonstrate that PK11195 acts on a mitochondrial target in order to facilitate the induction of apoptosis. This novel property of compounds of the isoquinolinecarboxamide family represents an opportunity for overcoming resistance to chemotherapy and to radiotherapy, and in particular for facilitating the induction of cell death.

EXAMPLE 1

Cells and Cell Cultures

The cell lines of the thymocyte hybridomas from 4- to 6-week-old Balb/c mice and of the 2B4.11 T-cells were transfected with the vector SFFV.neo containing the human bcl-2 gene or only the gene for resistance to neomycin (neo) (Green et al. 1994). The leukemic WEHI231 B-cells were transfected with the human bcl-2 gene or with a control neo vector (Cuende et al. 1993) and the human CEM-C7.H2 T-cells of lymphoblastic leukemia (Strasser-Wozak, 1995) were cultured in RPMI 1640 containing 10% FCS, antibiotics and L-glutamine.

EXAMPLE 2

Induction of Apoptosis

The abovementioned cells ($5-10\times10^5$/ml) were cultured in the presence of the indicated amount of PK11195, diazepam (Sigma), dexamethazone (1 µM, Sigma) RU24858 (1 µM, Roussel-Uclaf), the glucocorticoid receptor antagonist RU38486 (1 µM, Roussel-Uclaf), doxorubicin (1 µg/ml, Pharmacia), etoposide (10 µM/ml, Sigma), cytosine arabinoside (10 µg/ml, Upjohn), cyclosporin A (10 µM, Sandoz), ceramide C8 (25 µM, Biomol, Plymouth Meeting, PA), or treatment by γ-irradiation (10 Gy). After the intervals indicated, the cells were recovered and the characteristics associated with apoptosis were tested.

EXAMPLE 3

Quantification of the Parameters Associated with Apoptosis by Flow Cytometry

Following the procedures published (Marchetti et al. 1996b, Zamzami et al. 1995 and Kroemer et al. 1997c), the following fluorochromes were used in order to determine the various changes associated with apoptosis:

3,3'-dihexyloxacarbocyanine iodide (DiOC$_6$, 20 nM, Bernadi et al. 1996) for the determination of $\Delta\Psi_m$ hydroethidine (HE, 4 µM) for the determination of the generation of superoxide anion annexin V conjugated with FITC (1 µg/ml, Nexins Research, Hoeven, The Netherlands) for the determination of the exposure of phosphatidylserine (PS) on the outer plasma membrane propidium iodide (PI) for the staining of cells permeabilized with ethanol in order to determine the frequency of the hypoploid cells.

All of the experiments were carried out at least three times and lead to similar results. The typical results obtained are shown in the various figures. The statistical significance of the results was calculated using the Student test.

EXAMPLE 4

Process for Preparing N,N-diethylcarbamate Phenyl-3 Naphtyle-1 (Melting Point: 74° C.)

This compound is prepared as described in EP 210084A1 in Ex. 63, page 61, 1. 19–31, incorporated in the description by reference.

EXAMPLE 5

Process for Preparing N,N-diethyl α-methyl Phenyl-2 Quinazoline-4 Propanamide (Melting Point: 124° C.)

This compound is prepared as described in EP 210084A1 in Ex. 7, page 20, 1. 6–14, incorporated herein by reference.

EXAMPLE 6

Process for Preparing N-methyl N-phenyl Phenyl-2 Quinazoline-4 Propanamide (Melting Point: 116° C.)

This compound is prepared as described in EP210084A1 in Ex. 8; page 21, 1.15–p.22, 1.11 together with p.20, 1.6–14, incorporated herein by reference.

EXAMPLE 7

Process for Preparing N,N-diethyl (Nitro-4 Phenyl)-2 Quinazoline-4 Propanamide (Melting Point: 168° C.)

This compound is prepared as described in EP 210084A1 in Ex. 11, p.23,1.20—p.24,1.24 together with p.20, 1.6–14; incorporated herein by reference.

EXAMPLE 8

Process for Preparing N,N-diéthyl [(Phényl-2 Trifluorométhyl-8 Quinolinyl-4)oxy]-2 Propanamide (Melting Point: 146° C.)

This compound is prepared as described in EP 210084A1 in Ex 84; p.72,1.28–p.73,1.9 together with p.55, 1.1–14; incorporated herein by reference.

EXAMPLE 9

Process for Preparing N,N-diethyl (Methoxy-3 Phenyl)-2 Quinazoline-4 Propanamide (Melting Point: 87° C.)

This compound is prepared as described in EP 210084A1 in Ex. 2; p.14, 1.11–19 together with p.13,1.33–p.14, 1.10; incorporated herein by reference.

EXAMPLE 10

Process for Preparing N,N-diethyl Phenyl-3 Isoquinoleine-1 Propanamide (Melting Point: 58° C.).

This compound is prepared as described in EP 210084A1 in Ex. 4; p.17, 1.6–15 together with p.13, 1.33–p.14, 1.10; incorporated herein by reference.

EXAMPLE 11

Process for Preparing N-methyl N-(methyl-1 Propyl) Phenyl-7 Benzo[b]thiophenecarboxamide-5 (Melting Point: 105° C.).

This compound is prepared as described in EP 248 734B1 in Ex.2; p.5,1.39–60 together with Ex. 1, p. 5, 1. 6–37); incorporated herein by reference.

EXAMPLE 12

Process for Preparing N,N-diethyl Phenyl-3 Naphtalenecarboxmide-1 (Melting Point: 65° C.).

This compound is prepared as described in EP 112776B1 in Ex. 20; p.11, 1.25–35 together with p,8, 1.3–14; incorporated herein by reference.

EXAMPLE 13

Process for Preparing N-methyl N[methyl-1 Propyl] (chloro-2 Phenyl)-1 Isoquinoleinecarboxamide-3 (Melting Point: 136° C.).

This compound is prepared as described in EP 094271B1 in Ex.21; p.7, col. 12, 1.57–p.8, col. 13, 1.2 together with p.6, col.9, 1.32–p.6, col.9, 1.54; incorporated herein by reference.

EXAMPLE 14

Biological Activity

The biological activity of the compounds according to the present invention can be illustrated as follows (the above mentioned documents are incorporated in the description by reference):

A: Assay for Apoptosis Induction in a Cell Population

To quantify in a cell population the number of apoptotic cells according to their DNA content, an assay method which is based on FACS analysis (fluorescence activated cell sorting) and which uses cell fluorescence labelling with two intercalating agents has been adapted from the method described by Pollack A. and Ciancio G. (Pollack A et Ciancio G.In: Flow Cytometry, Darzynkiewicz Z, Crissman H A (eds). Academic Press, San Diego, Calif., 1991, pp 19–24). After trypsinisation, cells were rinsed with PBS (<<Phosphate Buffer Saline purchased from, for example, Gibco BRL) and fixed in 1 ml cold ethanol during 30 minutes. Cells were then rinsed twice in 2 ml PBScontaining 0.5% Tween 20, then resuspended in 1 ml coloration medium (PBS-Tween 20 0.5% containing 1 mg/ml boiled Rnase, 10 µg/ml Propidium iodide and 4 µg/ml DAPI-4', 6-diamidino-2-phenylindole dihydrochloride).FACS analysis was run after UV excitation. Studies were run with cell population grown in Nunc 6-well plates seeded with 100 000 cells by well in 2 ml complete medium, various compounds inducing or facilitating apoptose being incorporated 36 hours after seeding and FACS analysis being carried out between 24 and 48 h after adding the compound(s).

B: Assay Method for Inhibition of Bcl2-dependent Anti-apoptotic Activity in a Cell Line that Conditionnally Overexpresses Bcl2

By means of stable transfection techniques and by using selection agents such as neomycin, hygromycin, zeocin or puromycin, clones derived for instance from NCI-H 11299 cell line (obtained from ATCC) can be established in order to have a conditional expression of Bcl2 strictly depending on tetracyclin or anhydrotetracyclin concentration in the culture medium. To do that, one can use the technique described by Gossen and Bujard (Gossen M & Bujard H. (1992). *Proc Natl Acad Sci U S A*, 89, 5547–51 Nucleic Acids Res 1993 Sep 11;21(18):4411–2), with the possibility to adapt it while keeping tile features of the transcriptional regulation system described by this authors. We have been able to establish clones that overexpress Bcl2 protein in absence of tetracyclin or anhydrotetracyclin in culture medium, whereas in presence of 0.5 mg/l anhydrotetracyclin, the protein was not detectable by western blotting by using anti-Bcl2 antibody, clone 124 purchased from DAKO and by using a protocol described by Venot et al. (Venot, C., Maratrat, M., Dureuil, C., Conseiller, E., Bracco, L., and Debussche, L. 1998. EMBO J. 17:4668–4679).

By using above-mentioned procedure, we have been able to characterize clones which exhibit, in absence of tetracyclin in culture medium, significantly lower sensitivity to apoptosis induction by a range of concentrations of apoptosis inducing agents than in presence of tetracyclin, which means when they overexpress Bcl2 protein rather than they do not. Apoptosis inducing agents tested have been for example adriamycin (10–100 µg/ml), terbutyl-hydroperoxide (25–100 µM), vincristine (0.03–0.003 µg/ml) and camptothecin (0.01–0.1 µg/ml). To quantify apoptosis induction, one can for example use the assay method described in A.

One possible way to assay inhibition of anti-apoptotic activity in a conditionally Bcl2 overexpressing cell line, this inhibition being due to treatment which can be for example incorporation of a chemical compound, can be to quantify, by using assay method of A, the percentage of apoptosis induction in a cell population coming from, for example, one of the above-pmentioned clones, in the 4 following situations:

1) The chemical compound to be evaluated is incorporated in culture medium with an apoptosis inducing agent such as for instance one of the above-mentioned agents and the clone is grown in absence of tetracyclin or anhydrotetracyclin, which means when it overexpress Bcl2. In this situation, the percentage of apoptotic cells P1 is determined.

2) The same apoptosis inducing agent as the one used in situation 1 is incorporated alone in the culture medium and the clone is grown in absence of tetracyclin or anhydrotetracyclin, which means when it overexpress Bcl2. In this situation, the percentage of apoptotic cells P2 is determined.

3) The chemical compound to be evaluated is incorporated in culture medium with the same apoptosis inducing agent as the one used in the situation 1 and the clone is grown in presence of tetracyclin (1 µg/ml) or anhydrotetracyclin(0.5 µg/ml), which means when it does not overexpress Bcl2. In this situation, the percentage of apoptotic cells P3 is determined.

4) The chemical compound is incorporated alone in the culture medium and the clone is grown in presence of tetracyclin (1 µg/ml) or anhydrotetracyclin(0.5 µg/ml), which means when it does not overexpress Bcl2. In this situation, the percentage of apoptotic cells P4 is determined.

One can calculte ratio $R=100\times(P1-P2)/(P3-P4)$. When $R=100$, inhibition of anti-apoptotic activity due to Bcl2 overexpression is 100% at the concentration of the chemical compound tested. When $R=0$, the compound does not inhibit this activity at the tested concentration. A series of results can be obtained from a range of concentrations of tested compound. One can calculate from these results an IC50. Several compounds can be then compared according to their relative IC50s. We will say for instance that a compound A is twice more active than a compound B if IC50 value that displays A is twice lower than IC50 value that displays B. IC50 values can depend on clone used, the apoptosis inducing agent used and the apoptosis inducing agent concentration used.

C:

Using the technique described in part B, it has enabled the determination of IC50 smaller than or about 50 µM for the PK1195 compound and the compounds from general formulas II, II, IV, V.

Advantageously, the compounds of general formula II, III, IV may be at least 5 times more active than the PK1195 compound.

Preferentially, compounds from examples 4 to 12 as described above are more active than the PK1195 compound.

Within the general formula (II), the following compounds are preferred:

N,N-diethylcarbamate de phenyl-3 naphtyle-1
N,N-diethyl α-methyl phenyl-2 quinazoline-4 propanamide
N-methyl N-phenyl phenyl-2 quinazoline-4 propanamide
N,N-diethyl (nitro-4 phenyl)-2 quinazoline-4 propanamide
N,N-diéthyl [(phényl-2 trifluorométhyl-8 quinolinyl-4) oxy]-2 propanamide
N,N-diethyl (methoxy-3 phenyl)-2 quinazoline-4 propanamide
N,N-diethyl phenyl-3 isoquinoleine-1 propanamide Within the general formula (III), the following compounds are preferred:
N-methyl N-(methyl-1 propyl) phenyl-7 benzo[b] thiophenecarboxamide-5

Within the general formula (IV), the following compounds are preferred:
N,N-diethyl phenyl-3 naphtalenecarboxamide-1

Within the general formula (V), the following compounds are preferred:
N-methyl N[methly-1 propyl] (chloro-2 phenyl)-1 isoquinoleinecarboxamide-3

REFERENCES

Bernardi, P., and Petronilli, V. (1996). The permeability transition pore as a mitochondrial calcium release channel; a critical appraisal. J. Bioenerg. Biomembr. 28, 129–136.

Beutner, G., Ruck, A., Riede, B., Welte, W., and Brdiczka, D. (1996). Complexes between kinases, mitochondrial porin, and adenylate translocator in rat brain resemble the permeability (transition pore. FEBS Lett. 396, 189–195.

Boise, L. H., and Thompson, C. B. (1997). Bcl-XL can inhibit apoptosis in cells that have undergone Fasinduced protease activation. Proc. Natl. Acad. Sci, USA 94, 3759–3764.

Carayon, P., Portier, M., Dussossoy, D., Bord, A., Petitpretre, G., Canat, X., Le Fur, G., and Casellas, P. (1996). Involvement of peripheral benzodiazepine receptors in the protection of hematopoietic cells against oxygen radical species. Blood 87, 3170–3178.

Cuende, E., Alés-Martinez, J. E., Ding, L., Gonzalez-Garcia, M., Martinez-A., C., and Nunez, G. (1993). Programmed cell death by Bcl-2-dependent and -independent mechanisms in B cell lymphoma cells. EMBO J. 12, 1555–1560.

De Jong, D., Prins, F. A., Mason, D. Y., Reed, J. C., van Ommen, G. B., and Kluin, P. M. (1994). Subcellular localization of the Bcl-2 protein in malignant and normal lymphoid cells. Cancer Res. 54, 256–260.

Decaudin, D., Geley, S., Hirsch, T., Castedo, M., Marchetti, P., Macho, A., Kofler, R., and Kroemer, G. (1997). Bcl-2 and Bcl-XL antagonize the mitochondrial dysfunction preceding nuclear apoptosis induced by chemotherapeutic agents. Cancer Res. 57, 62–67.

Ellerby, H. M., Martin, S. J., Ellerby, L. M., Naiem, S. S., Rabizadeh, S., Salvese, G. S., Casiano, C. A., Cashman, N. R., Green, D. R., and Bredesen, D. E. (1997). Establishment of a cell-free system of neuronal apoptosis: comparison of premitochondrial, mitochondrial, and postmitochondrial phases. J. Neurosci. 17, 6165–6178.

Evtodienki, Y. V., Teplova, V. V., Sidashi, S. S., Ichas, F., and Mazat, J.-P. (1996). Microtubule-active drugs suppress the closure of the permeability transition pore in tumour mitochondria. FEBS Lett. 393, 86–88.

Green, D. R., Mahboubi, A., Nishioka, W., Oja, S., Echeveiri, F., Shi, Y., Glynn, J., Yang, Y., Ashwell, J., and Bissonnette, R. (1994). Promotion and inhibition of activation-induced apoptosis in T-cell hybridomas by oncogenes and related signals. Immunol. Rev. 142, 321–342.

Haldar, S., Chintapalli, J., and Croce, C. M. (1996). Taxol induces bcl-2 phosphorylation and death of prostate cancer cells. Cancer Research 56, 1253–1255.

Haldar, S., Jena, N., and Croce, C. M. (1995). Inactivation of Bcl-2 by phosphorylation. Proc. Natl. Acad Sci. USA 92, 4507–4511.

Hirsch, T., Marchetti, P., Susin, S. A., Dallaporta, B., Zamzami, N., Marzo, I., Geuskens, M., and Kroemer, G. (1997). The apoptosis-necrosis paradox. Apoptogenic proteases activated after mitochondrial permeability transition determine the mode of cell death. Oncogene 15, 1573–1582.

Hortelano, S., Dallaporta, B., Zamzami, N., Hirsch, T., Susin, S. A., Marzo, I., Bosca, L., and Kroemer, G. (1997). Nitric oxide induces apoptosis via triggering mitochondrial permeability transition. FEBS Lett. 410, 373–377.

Huang, D. C. S., Cory, S., and Strasser, A. (1997). Bcl-2, Bcl-XL, and adenovirus protein E1B19kD are functionally equivalent in their ability to inhibit cell death. Oncogene 14, 405–414.

Ichas, F., Jouavill, L. S., and Mazat, J.-P. (1997). Mitochondria are excitable organelles capable of generating and conveying electric and calcium currents. Cell 89, 1145–1153.

Joseph-Liauzun, E., Farges, R., Delmas, P., Ferrara, P., and Loison, G. (1997). The M-r 18,000 subunit of the peripheral-type benzodiazepine receptor exhibits both benzodiazepine and isoquinolinecarboxamide binding sites in the absence of the voltage-dependent anion channel or of the adenine nucleotide carrier. J. Biol. Chem. 272, 28102–28106.

Kantrow, S. P., and Piantadosi, C. A. (1997). Release of cytochrome c from liver mitochondria during permeability transition. Biochem. Biophys. Res. Comm. 232, 669–671.

Kinnally, K. W., Lohret, T. A., Campo, M. L., and Mannella, C. A. (1996). Perspectives on the mitochondrial multiple conductance channel. J. Bioenerg. Biomembr. 28, 115–123.

Kinnally, K. W., Zorov, D. B., Antonenko, Y. N., Snyder, S. H., McEnery, M. W., and Tedeschi, H. (1993). Mitochondrial benzodiazepine receptor linked to inner membrane ion channels by nanomolar actions of ligands. Proc. Natl. Acad. Sci. USA 90, 1374–1378.

Kluck, R. M., Bossy-Wetzel, E., Green, D. R., and Newmeyer, D. D. (1997). The release of cytochrome c from mitochondria: a primary site for Bcl-2 regulation of apoptosis. Science 275, 1132–1136.

Kroemer, G., Zamzami, N., and Susin, S. A. (1997a). Mitochonidrial control of apoptosis. Immunol. Today 18, 44–51.

Kroemer, G. (1997b). The proto-oncogene Bcl-2 and its role in regulating apoptosis. Nature Medicine 3, 614–620.

Kroemer, G., Lisardo, B., Zamzami, P., Hortelano, S., and Martinez-A., C. (1997c). Detection of apoptosis and apoptosis associated alterations. "The Immunology Methods Manual" (Lefkovitz, R. Ed.); Academic Press, Chapter 14.2., pp. 1111I–1125.

Leist, M., Single, B., Castoldi, A. F., Kuhnle, S., and Nicotera, P. (1997). Intracellular adenosine triphosphate (ATP) concentration: a switch in the decision between apoptosis and necrosis. J. Exp. Med. 185, 1481–1486.

Liu, X., Kim, C. N., Yang, J., Jemmerson, R., and Wang, X. (1996). Induction of apoptotic program in cell-free extracts: requirement for dATP and cytochrome C. Cell 86, 147–157.

Marchetti, P., Castedo, M., Susin, S. A., Zamzami, N., Hirsch, T., Haeffner, A., Hirsch, F., Geuskens, M., and Kroemer, G. (1996a). Mitochondrial permeability transition is a central coordinating event of apoptosis. J. Exp. Med 184, 1155–1160.

Marchetti, P., Hirsch, T., Zamzami, N., Castedo, M., Decaudin, D., Susin, S. A., Masse, B., and Kroemer, G. (1996b). Mitochondrial permeability transition triggers lymphocyte apoptosis. J. Immunol, 157, 4830–4836.

McEnery, M. W., Snowman, A. M., Trifiletti, R. R., and Snyder, S. H. (1992). Isolation of the mitochondrial benzodiazepine receptor: Association with the voltage-dependent anion channel and the adenine nucleotide carrier. Proc. Natl. Acad. Sci. USA 89,3170–3174.

Nicotera, P., and Leist, M. (1997). Energy supply and the shape of death in neurons and lymphoid cells. Cell Death Diff: 4, 435–442.

O'Gorman, E., Beutner, G., Dolder, M., Koretsky, A. P., Brdiczka, D., and Wallimann, T. (1997). The role of creatine kinase in inhibition of mitochondrial permeability transition. FEBS Lett. 414, 253–257.

Pastorino, J. G., Simbula, G., Yamamoto, K., Glascott, P. A. J., Rothman, R. J., and Farber, J. L. (1996). The cytotoxicity of tumor necrosis factor depends on induction of the mitochondrial permeability transition. J. Biol. Chem. 271, 29792–29799.

Polyak, K., Xia, Y., Zweier, J. L., Kinzler, K. W., and Vogelstein, B. (1997). A model for p53-induced apoptosis. Nature 389, 300–305. Reed, J. C. (1997). Double identity for proteins of the Bcl2 family. Nature 387, 773–776.

Ripond, J., Mattei, M. G., Kaghad, M., Dumont, X., Guillemot, J. C., Lefur, G., Caput, D., and Ferrara, P. (1991). Molecular cloning and chromosomal localization of a human peripheral type benzodiazepine receptor. Eur. J. Biochem. 2, 305–311.

Schulze-Osthoff, K., Krammer, P. H., and Droge, W. (1994). Divergent signalling via APO-1/Fas and the TNF receptor, two homologous molecules involved in physiological cell death. EMBO J. 13, 4587–4596.

Strasser, A., Harris, A. W., Huang, D. C. S., Krammer, P. H., and Cory, S. (1995). Bcl-2 and Fas/APO-1 regulate distinct pathways to lymphocyte apoptosis. EMBO J. 14, 6136–6147.

Strasser-Wozak, E., Hattmannstorfer, R., Hala, M., Hartmann, B. L., Fiegl, M., Geley, S., and Kofler, R. (1995). Splice site mutation in the glucocorticoid receptor gene causes resistance to glucocorticoid-induced apoptosis in a human acute leukemic cell line. Cancer Res 55, 348–353.

Susin, S. A., Zamzami, N., Castedo, M., Hirsch, T., Marchetti, P., Macho, A., Daugas, E., Geuskens, M., and Kroemer, G. (1996a). Bcl-2 inhibits the mitochondrial release of an apoptogenic protease. J. Exp. Med. 184, 1331–1342.

Susin, S. A., Zamzami, N., Castedo, M., Daugas, E., Wang, H.-G., Geley, S., Fassy, F., Reed, J., and Kroemer, G. (1997b). The central executioner of apoptosis. Multiple links between protease activation and mitochondria in Fas/Apo-1/CD95- and ceramide-induced apoptosis. J. Exp. Med 186, 25–37.

Vander Heiden, M. G., Chandal, N. S., Williamson, E. K., Shcumacker, P. T., and Thompson, C. B. (1997). Bcl-XL regulates the membrane potential and volume homeostasis of mitochondria. Cell 91, 627–637.

Yang, J., Liu, X., Bhalla, K., Kim, C. N., Ibrado, A. M., Cai, J., Peng, T.-I., Jones, D. P., and Wang, X. (1997). Prevention of apoptosis by Bcl-2: release of cytochrome c from mitochondria blocked. Science 275, 1129–1132.

Yasuhara, N., Sahara, S., Kamada S, Fguchi, Y., and Tsujimato, Y. (1997). Evidence against a functional site for Bcl-2 downstream of caspase cascade in preventing apoptosis. Oncogene 15, 1921–1928.

Zamzami, N., Marchetti, P., Castedo, M., Decaudin, D., Macho, A., Hirsch, T., Susin, S. A., Petit, P. X., Mignotte, B., and Kroemer, G. (1995). Sequential reduction of mitochondrial transmembrane potential and generation of reactive oxygen species in early programmed cell death. J. Exp. Med 182, 367–377.

Zamzami, N., Susin, S. A., Marchetti, P., Hirsch, T., Gomez-Monterrey, I, Castedo, M., and Kroemer, G. (1996). Mitochondrial control of nuclear apoptosis. J. Exp. Med. 183, 1533–1544.

Zisterer, D. M., and Williams, D. C. (1997). Peripheral-type benzodiazepine receptors. Gen. Pharmacol. 29, 305–314.

Zoratti, M., and Szabo, I. (1995). The mitochondrial permeability transition. Biochem. Biophys. Acta-Rev. Biomcmbranes 1241, 139–176.

What is claimed is:

1. Combination product comprising at least one compound with affinity for the mitochioidrial benzodiazepine receptor, and at least one apoptosis-inducing agent for simultaneous or separate use or for use spread out over time, which is intended for the treatment of cancer.

2. Product according to claim 1, wherein the compound is selected from a compound of the formula I:

I in which
R1 is a linear or branched C1–C6 lower alkyl group,
R2 is a linear or branched C1–C6 lower alkyl group,
R3 is a halogen atom,
and R4 is a hydrogen or halogen atom,
the groups R1, R2, R3 and R4 being chosen independently of each other.

3. Product according to claim 2, wherein the compound is PK11195:

1-(2-chlorophenyl)-N-methyl-N-(1-methylpropyl)-3-isoquinoline-carboxamide.

4. Product according to claim 1, wherein the compound is selected from a compound of the formula II:

II in which
A represents a nitrogen atom or a CH group,
B represents a nitrogen atom or a CH group,
V and W, which may be identical or different, represent hydrogen atoms or halogen atoms, alkyl or alkoxy groups comprising 1 to 3 carbon atoms, or nitro or trifluoromethyl groups,
Z is fixed in an ortho or para position relative to B and represents a phenyl, thienyl or pyridyl radical, or a phenyl radical substituted with one or two substituents taken from halogen atoms, alkyl and alkoxy groups comprising 1 to 4 carbon atoms, and trifluoromethyl or nitro groups,
the chain —X—$(CH_2)_n$—$(CHR)_m$—$(CHR)_m$—$CONR_1R_2$ is fixed in an ortho or para position relative to B,
R represents a hydrogen atom or an alkyl group comprising 1 to 3 carbon atoms, $R_1$ and $R_2$ which may be identical or different, represent a linear or branched alkyl group comprising 1 to 6 carbon atoms, a cycloalkyl group comprising 3 to 6 carbon atoms, a phenyl group, a phenylalkyl or cycloalkylalkyl group in which the alkyl part comprises 1 to 3 carbon atoms and the cycloalkyl part comprises 3 to 6 carbon atoms, an alkenyl group comprising 3 to 6 carbon atoms on condition that the double bond is not located in position 1,2 relative to the nitrogen atom, $R_1$ and $R_2$ can also form, together with the nitrogen atom to which they are attached, a pyrrolidine, piperidine, morpholine or thiomorpholine ring, X represents a group $CH-R_4$, $N-R_1$, SO or $SO_2$ or an oxygen or sulfur atom, $R_3$ represents a hydrogen atom or an alkyl group comprising 1 to 3 carbon atoms, $R_4$ represents an alkyl group comprising 1 to 3 carbon atoms, m is equal to 0 or 1, n is equal to 0, 1 or 2, it being understood that when X represents a group SO, $SO_2$ or $N-R_4$, the sum m+n is at least equal to 1, it being understood that when A and B each represent a nitrogen atom and Z is in the para position relative to B, X cannot represent a group $CH-R_3$, it being understood that when A represents a CH group, B represents a nitrogen atom, Z is an ortho position relative to B, X represents an oxygen atom and R represents a hydrogen atom, the sum m+n is other than 1, with the exception of 2-phenyl-4-quinolyl N,N-dimethylcarbamate.

5. Product according to claim 1, wherein said apoptosis-inducing agent is selected from agents which damage DNA, natural or synthetic ligands of the glucocorticoid receptor, or pro-apoptotic second messengers.

6. Product according to claim 5, wherein said agent is selected from γ-radiations, etoposide, doxorubicin, dexamethasone, ceramide, ceramide C8, and lonidamine.

7. Product according to claim 5, wherein said proapoptotic second messenger is selected from glucocorticoid, from alkylating agents, nitrogen mustards, cyclophosphamide, platinum complexes, cisplatin, ethyleneimine, dimethane sulfonoxyalkane, or piperazine, from topoisomerase inhibitors, topoisomerase-2 inhibitors, anthracyclines, epipodophyllotoxins, etoposide, topoisomerase 1 inhibitors, camptothecin, from antimetabolites, antifolates, methotrexate, antipurines, 6-mercaptopurine, antipyrimidines, 5-fluorouracil, from antimitotic agents, vinca alkaloids, taxoids, taxol, taxotere, and from various cytolytic agents, bleomycin, dacarbazine, hydroxycarbamide, asparaginase, mitoguazone and plicamycin.

8. Product according to claim 1, wherein it also comprises a viral vector which contains a gene which codes for thymidine kinase.

9. A method of treating cancer comprising administering to a patient in need thereof a pharmaceutically effective amount of the product of claim 4 and a pharmaceutically acceptable carrier.

* * * * *